United States Patent [19]

Henning

[11] Patent Number: 4,881,537

[45] Date of Patent: Nov. 21, 1989

[54] SURGICAL INSTRUMENT, AND METHODS FOR FORMING A CHANNEL IN A FEMORAL CONDYLE INCLUDING RECONSTRUCTING AN ANTERIOR CRUCIATE LIGAMENT

[76] Inventor: Charles Henning, 7401 Pagent, Wichita, Kans. 67206

[21] Appl. No.: 232,427

[22] Filed: Aug. 10, 1988

[51] Int. Cl.⁴ .................. A61B 17/16; A61B 17/56
[52] U.S. Cl. ......................... 606/84; 623/13; 606/79; 606/85
[58] Field of Search ............. 128/303 R, 304, 305, 128/92 V, 92 VY, 92 VW, 92 VS, 92 VJ, 92 UD, 92 VL, 92 YF; 30/279 R, 280, 282, 287–289, 299, 304, 346.57, 353, 356, 357; 623/13

[56] References Cited

U.S. PATENT DOCUMENTS

| | | | |
|---|---|---|---|
| 1,628,315 | 5/1927 | Hamilton | 30/280 |
| 2,770,878 | 11/1956 | Rosenberger | 30/280 |
| 3,639,982 | 2/1972 | O'Neal | 30/279 |
| 3,667,470 | 6/1972 | Rubin | 128/304 |
| 3,896,500 | 7/1975 | Rambert et al. | 128/924 YF |
| 4,239,045 | 12/1980 | Schlein | 128/305 |
| 4,246,660 | 1/1981 | Wevers | 128/92 YF |
| 4,585,458 | 4/1986 | Kurland | 623/13 |
| 4,600,005 | 9/1986 | Hendel | 128/304 |
| 4,632,100 | 12/1986 | Somers et al. | 623/13 X |
| 4,772,286 | 9/1988 | Goble et al. | 128/92 YF |

Primary Examiner—Richard J. Johnson
Assistant Examiner—Kevin G. Rooney
Attorney, Agent, or Firm—John W. Carpenter

[57] ABSTRACT

A surgical instrument having a cutting end which includes a pair of grooves to provide a structure having a pair of opposed flanges. The back of the surgical instrument has a back channel. A pair of cutting edges are provided on the surgical instrument. The cutting edges are generally offset and parallel with respect to each other. A method for forming a channel in a femoral condyle of a knee joint of a person, and a method for reconstructing an anterior cruciate ligament of a knee joint of a person. The methods comprise using the surgical instrument in an inside-out fashion, as opposed to an outside-in fashion, in order to cut a trough into a femoral condyle.

19 Claims, 3 Drawing Sheets

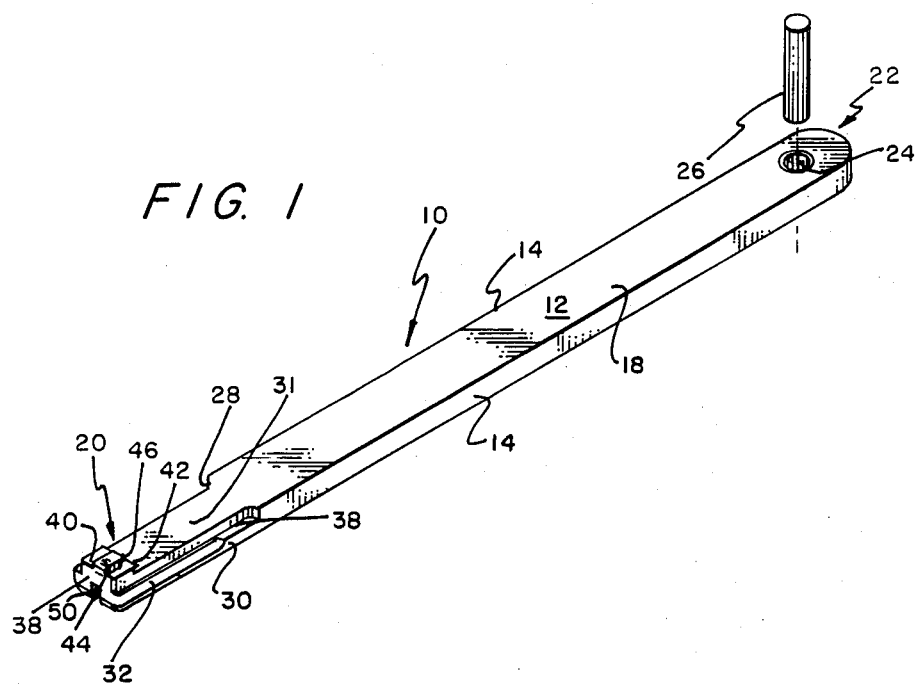
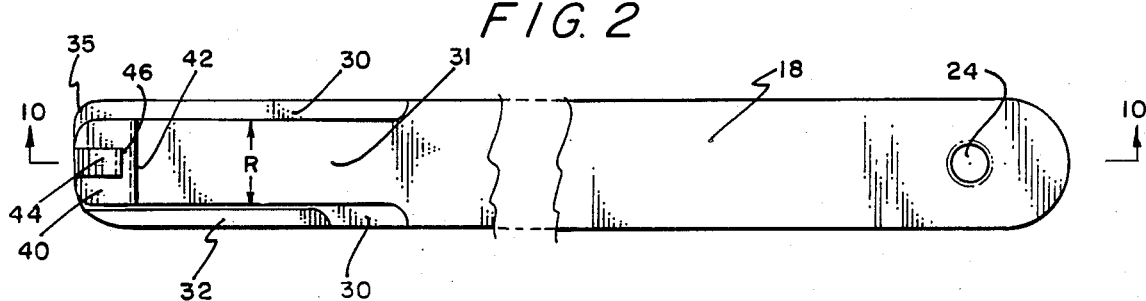
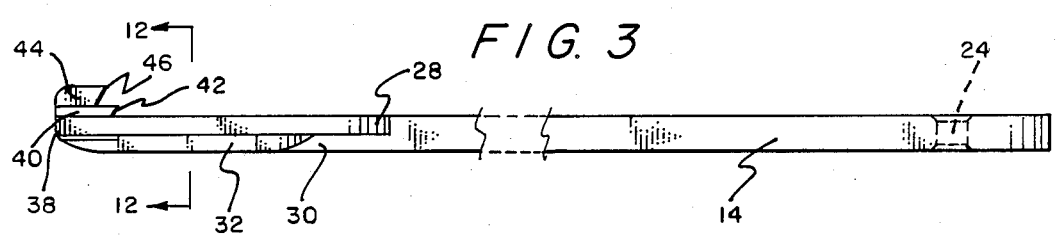
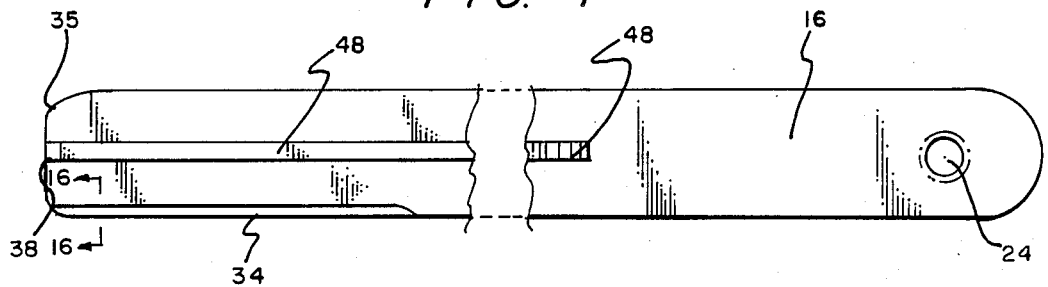

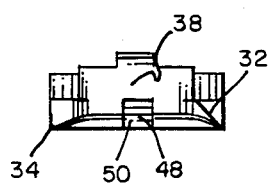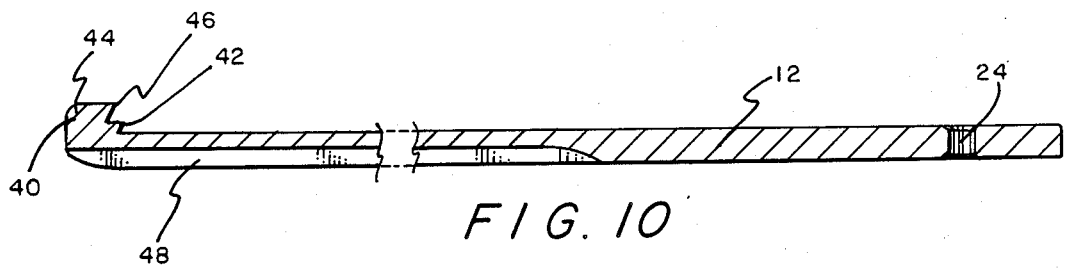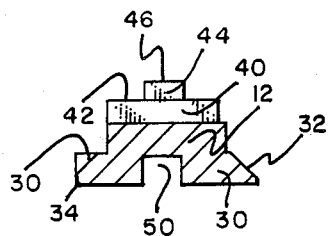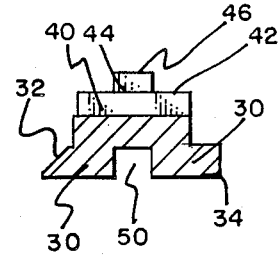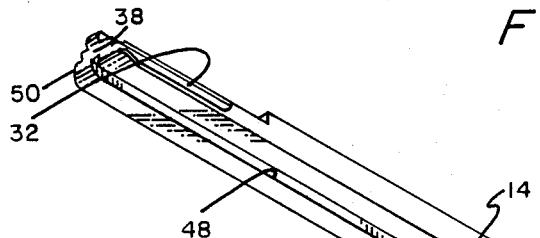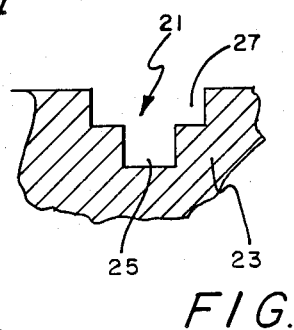

4,881,537

SURGICAL INSTRUMENT, AND METHODS FOR FORMING A CHANNEL IN A FEMORAL CONDYLE INCLUDING RECONSTRUCTING AN ANTERIOR CRUCIATE LIGAMENT

BACKGROUND OF THE INVENTION

1. Field of the Invention

This invention is related to a surgical instrument. More specifically, this invention provides a surgical instrument which is employed to form a channel in a femoral condyle of a knee joint and to reconstruct an anterior cruciate ligament in the knee joint of a person.

2. Description of the Prior Art

A patentability investigation was conducted and the following patents were discovered: U.S. Pat. Nos. 872,567 to Langstaff; 1,080,929 to Romeo; 1,192,654 to Uddenberg; 2,876,777 to Kees, Jr.,; 3,667,470 to Rubin; and 4,221,222 to Detsch. None of the foregoing prior patents teach or suggest the particular surgical instrument of this invention. Nor do any of the prior art patents teach or suggest the particular methods of this invention.

SUMMARY OF THE INVENTION

The present invention accomplishes its desired objects by broadly providing a surgical instrument that has a shank means with a pair of shank sides, a shank back, and a shank front. The shank means additionally includes a cutting end means and a handle end means. The cutting end means has a pair of grooves in the shank front and along the pair of shank sides such that the cutting end means has a structure defining a pair of opposed flanges. The shank handle end means has a handle aperture wherethrough a pin or the like slidably passes in order to provide the engagement point of a commercially available slap or split hammer. The shank back has a back channel that substantially transverses the entire structure of the shank to terminate in an open shank end. Imposed on and secured to the shank front is a first cutting member having a first cutting edge. Imposed to and secured to the first cutting member is a second cutting member having a second cutting edge. The first and second cutting member are secured to the shank front on the cutting end means of the shank. One of the opposed flanges has a structure which includes a beveled edge. The first cutting edge and the second cutting edge are offset with respect to each other and are substantially parallel. The first cutting edge is longer than the second cutting edge.

The present invention also accomplishes its desired objects by providing a method for forming a channel in a femoral condyle of a knee joint of a person. The method comprises forming the surgical instrument of this invention. As previously indicated above, the surgical instrument has a channel in the back thereof, a cutting end means with a first cutting edge, a second cutting edge, and a pair of opposed flanges wherein one of the flanges has a beveled edge. After forming the surgical instrument of this invention, the method further comprises forming a surgical opening through a skin tissue or knee capsule that surrounds a knee joint of a person that is being operated on. The knee joint is well known to include a posterior femoral notch, a femoral metaphysis, a medial femoral condyle, and a femoral condyle. The method further comprises inserting the cutting end means through the surgical opening until the first and second cutting edges are disposed in the posterior femoral notch and against the femoral condyle and further until the beveled edge is flushed against the femoral metaphysis. Subsequently, a guide wire is inserted through the channel on the back of the surgical instrument and into the medial femoral condyle to be implanted therein. The surgical instrument is now in a posture to be operated in an inside-out procedure (as opposed to the conventional outside-in procedure). In the inside-out procedure, the surgical instrument is pulled along the guide wire outwardly and subsequently is pushed inwardly along the guide wire in a reciprocating fashion until the first and second cutting edges have cut a trough in the femoral condyle. In between the pulling and pushing of the surgical instrument along the guide wire and when the surgical instrument is outside of the surgical opening, femoral condyle debris should be removed from the first and second cutting edges. The channel formed has a lowermost channel having a width equal to the width of the second cutting edge, and an uppermost channel imposed over the lower channel and communicating therewith, having a width equal to the first cutting edge. The lowermost channel is for receiving sutures extending from a previously formed patellar bone block, and the upper channel is for receiving the patellar bone block itself.

The present invention still yet further accomplishes its desired objects by providing a method for reconstructing an anterior cruciate ligament of a knee joint of a person. This method comprises initially forming the surgical instrument of this invention as was previously indicated above, and subsequently forming a surgical opening through a skin tissue or knee capsule that surrounds the knee joint of a person. As was indicated, a person's knee joint comprises a posterior femoral metaphysis, a posterior femoral notch, a medial femoral condyle, a tibia, a lateral femoral condyle, and a distal femur. Subsequently to forming the surgical instrument and forming a surgical opening around the knee joint, the cutting end means of the surgical instrument is inserted through the surgical opening until the first and second cutting edges are disposed in the posterior femoral notch and against the lateral femoral condyle and further until the beveled edge is flushed against the posterior femoral metaphysis. A guide wire is subsequently inserted through the channel of the surgical instrument into the medial femoral condyle. The surgical instrument is then pulled along the guide wire causing the first cutting edge and the second cutting edge to cut and remove lateral femoral condyle bone fragments. These bone fragments are cleaned from the first and second cutting edges. The method additionally comprises reinserting the surgical instrument into the surgical opening such that the first and second cutting edges are against the lateral femoral condyle. This insertion step includes moving the surgical instrument along the guide wire while the same is in the channel. The steps of pulling the surgical instrument along the guide wire, removing femoral condyle debris from the cutting edges of the surgical instrument, and moving the surgical instrument through the surgical opening again and along the guide wire, are subsequently repeated until the desired channel is formed in the femoral condyle. As indicated, the desired channels comprise a suture channel and a bone block channel that is opposed to the suture channel and communicating therewith. The method additionally comprises the steps of forming a patellar bone block having sutures and securing an end of a patellar tendon to the patellar bone block. A tibia bone block with tibia sutures is formed and is connected to another end of the patellar tendon. The method additionally includes the steps of inserting a screw or pin means through the distal femur; disposing the sutures of the patellar bone block in the suture channel and the patellar bone block in the bone block channel; and securing the sutures to the screw or pin means. The tibia bone block is secured to the tibia by securing the tibia sutures to the tibia. Finally, the surgical opening is closed with the knee joint of a person having a reconstructed anterior cruciate ligament.

It is therefore an object of the present invention to provide a surgical instrument.

It is yet another object of the present invention to provide a method for reconstructing an anterior cruciate ligament of a knee joint of a person.

Still further objects of the invention reside in providing a method for forming a channel in a femoral condyle of a knee joint of a person.

These, together with the various ancillary objects and features which will become apparent to those skilled in the art as the following description proceeds, are attained by this novel surgical instrument and methods, a preferred embodiment being shown with respect to the accompanying drawings, by way of example only, wherein:

BRIEF DESCRIPTION OF THE DRAWINGS

FIG. 1 is a perspective view of the surgical instrument for operating on a right knee joint of a person;

FIG. 2 is a top plan view of the surgical instrument in FIG. 1;

FIG. 3 is a side elevational view of the surgical instrument of FIG. 2;

FIG. 4 is a bottom plan view of the surgical instrument of FIG. 2;

FIG. 9 is an end elevational view of the surgical instrument of FIG. 1;

FIG. 10 is a vertical sectional view taken in direction of the arrows and along the plane of line 10—10 in FIG. 2;

FIG. 11 is a vertical sectional view taken in direction of the arrows and along the plane of line 11—11 in FIG. 7;

FIG. 12 is a vertical sectional view taken in direction of the arrows and along the plane of line 12—12 in FIG. 3;

FIG. 13 is a perspective view of the underside of the surgical instrument of FIG. 1;

FIG. 14 is a plan view of a guide wire that is to be inserted or implanted into a medial femoral condyle in order to guide the surgical instrument as it cuts a channel into a femoral condyle;

FIG. 15 is a partial sectional view of a femoral condyle disclosing a channel or trough in the femoral condyle defined by a suture channel and a patellar bone block channel; and FIG. 16 is a partial sectional view taken in direction of the arrows and along the plane of line 16—16 in FIG. 4.

DETAILED DESCRIPTION OF THE INVENTION

Figure 5:
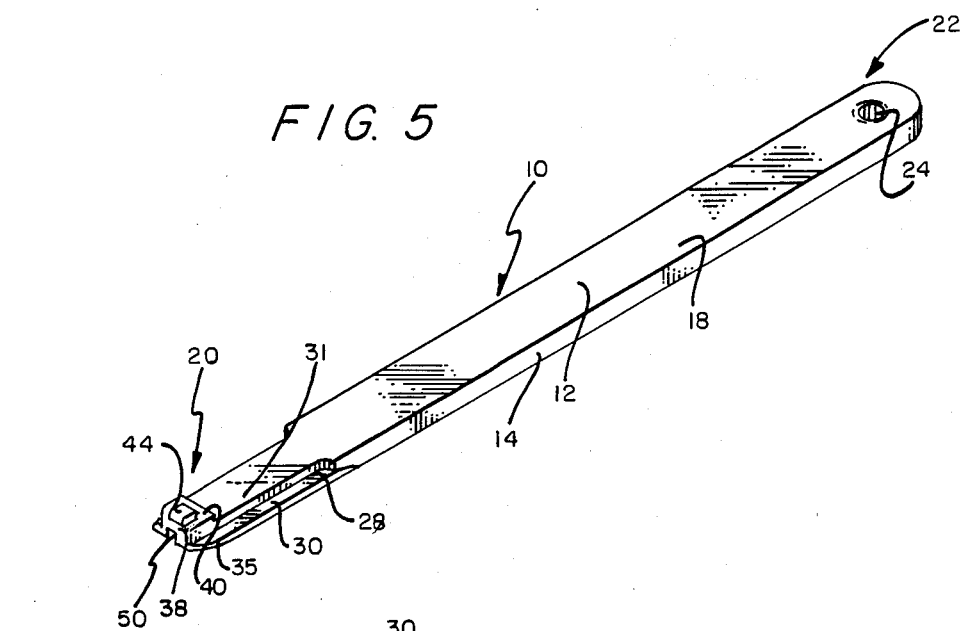
FIG. 5 is a perspective view of an embodiment of the surgical instrument that is employed in operating on the left knee joint of a person.

Referring in detail now to the drawings, wherein similar parts of the invention are identified by like reference numerals, there is seen the surgical instrument of this invention, generally illustrated as 10, which is employed for reconstructing the anterior cruciate ligament and is used as an inside-out procedure (instead of the usual outside-in procedure). The surgical instrument 10 has a shank 12 having a pair of sides 14—14, a back 16 and a front 18. The surgical instrument 10 has a cutting end, generally illustrated as 20, which is for forming or cutting a trough, groove, or the like, generally illustrated as 21 in FIG. 15, in a femoral condyle 23 (e.g. a lateral femoral condyle). The trough 21 produced in accordance with the use of the surgical instrument 10 of this invention has a suture channel 25 and a patellar bone block channel 27 where sutures secured to a patellar bone block and the patellar bone block itself (all not shown in the drawings) respectively lodge.

The shank 12 of the surgical instrument 10 has a hammer end generally illustrated as 22, which includes an aperture 24 wherethrough a pin 26 slidably lodges such that in operation of the surgical instrument 10, a commercially available slap or split hammer is allowed to engage the hammer end 22 to pull the surgical instrument 10 towards the operator to cut the trough 21 and clear femoral condyle 23 bone debris out of the trough 21, which lessens the risk of loose bone particles in a knee.

Figure 6:
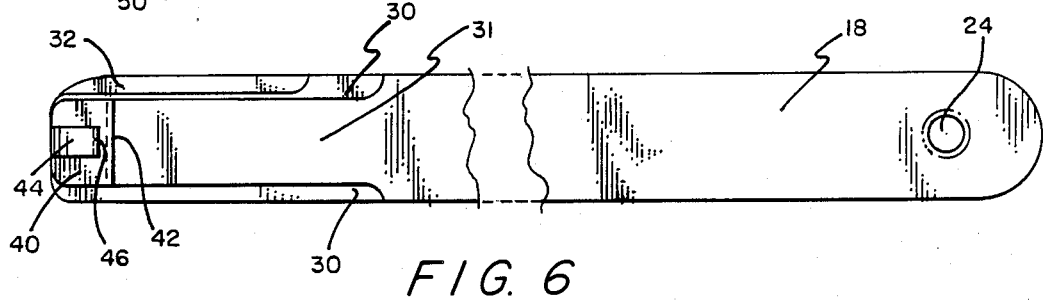
FIG. 6 is a top plan view of the surgical instrument in FIG. 5.
Figure 7:
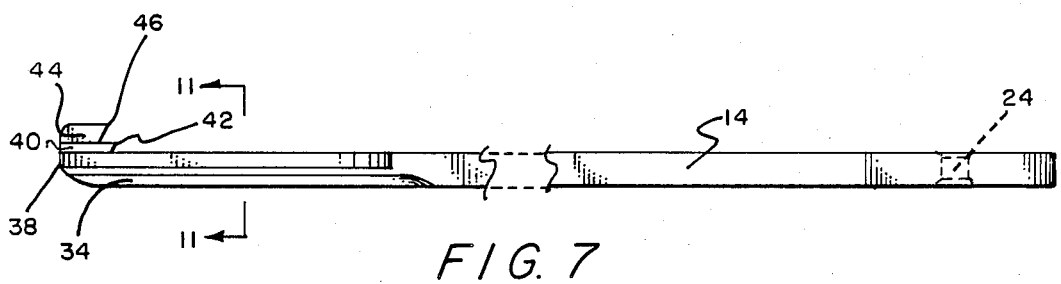
FIG. 7 is a side elevational view of the surgical instrument in FIG. 6.
Figure 8:
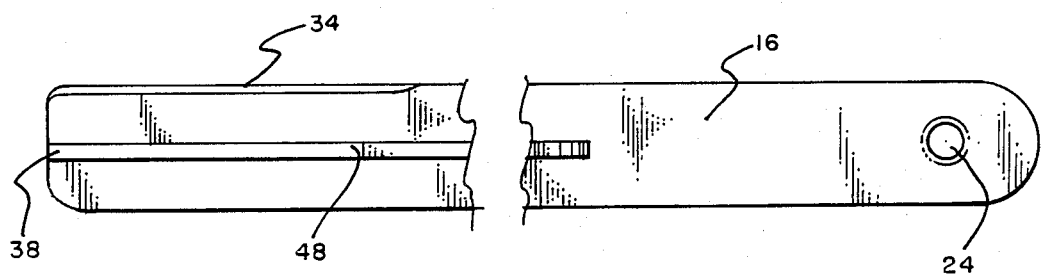
FIG. 8 is a bottom plan view of the surgical instrument of FIG. 6.

The cutter end 20 of the surgical instrument 10 comprises a pair of grooves, ridges, recesses, or the like, illustrated as 28—28, formed partly along and/or into the sides 14—14 and partly int he front 18 of the shank 12 such that a pair of flanges 30—30 is provided in the cutting end 20 in an opposed relationship with respect to each other. A residual structure portion 31 remains in the cutting end 20 disposed between the flanges 30—30 and has a width designated as R in FIG. 2. One of the flanges 30 is formed with a beveled edge, a tapering or sloping surface (or the like) 32. Similarly, the back of the flange 30 opposed to the flange 30 having the beveled edge 32 has a rounded (machined, or the like) edge 34 and a rounded, arcuate corner 35. Which of the flanges 30—30 having the beveled edge 32 or the rounded edge 34 and the rounded corner 35 depends on the embodiment of the invention. More specifically, the embodiment of the surgical instrument 10 in FIGS. 1–4 (i.e., the right knee embodiment) is to be employed when cutting into a femoral condyle 23 in a right knee. The embodiment of the surgical instrument 10 in FIGS. 5–8 (i.e., the left knee embodiment) is to be used when cutting into a femoral condyle 23 in a left knee. As best seen in FIGS. 2 and 6, the beveled edge 32 is placed or formed on or in one particular flange 30 for the right knee embodiment of FIG. 2, and in FIG. 6 for the left knee embodiment the beveled edge 32 is formed or placed on or in the flange 30 opposed to the flange 30 in FIG. 2 having the beveled edge 32. Similarly, as best seen in FIGS. 4 and 8, the rounded edge 34 and rounded corner 35 are placed or formed on or in the rear of one particular flange 30 for the right knee embodiment of FIG. 4, while in the left knee embodiment in FIG. 6, the rounded edge 34 and rounded corner 35 are placed or formed on or in the rear of flange 30 that is opposed to the flange 30 in FIG. 4 having the rounded edge 34 and rounded corner 35. Thus, for both embodiments of FIGS. 1-8, the beveled edge 32 is on or in the flange 30 opposed to the flange 30 having the rounded edge 34 and rounded corner 35, and vice versa.

Common to both embodiments of FIGS. 1-8 is the cutting end 20 terminating in a planar shank surface 38 (or a flat or planar end). Mounted on the cutting end 20 and on the front 18 of the shank 12 is a lower cutting member 40 having a lower cutting edge 42. Superimposed over and mounted to the lower cutting member 40 is an upper cutting member 44 having an upper cutting edge 46. Preferably, cutting edge 42 has the same width as the structured residual portion 31 and is thus equal to R, cutting edge 42 is wider or longer than cutting edge 46, and both are offset and parallelly disposed with respect to each other. As shown in FIGS. 1 and 3, the structure of the lower and uppeer cutting members 40 and 44 terminate in the planar shank surface 38.

The back 16 of the shank 12 is formed with a channel 48 that traverses a substantial portion of the back 16 and terminates in an open space 50 in the planar shank surface 38. Thus, channel 48 has an open end. The purpose of channel 48 is to receive and slidably house a guide wire 52 (see FIG. 14) therein that has been implanted into a medial femoral condyle. Guide wire 52 serves as a collimator or register such that in the inside-out procedure, the cutting members 40 and 44 are continually aligned with the initial started, cutting locus of the cutting members 40 and 44 cutting the trough 21 on or in the femoral condyle 23, as a substantial portion of the shank 12 slides along the implanted guide wire 52 while the latter is slidably disposed within the channel 48.

With continued reference to the drawings for operation of the surgical instrument 10 and the method for forming a channel or trough 21 in a femoral condyle 23 of a knee joint of a person, one of the embodiments of the surgical instrument 10 is formed as previously indicated. More specifically, the surgical instrument 10 should be formed with the back 16 having the channel 48, a cutting end means 20 with a first cutting edge 42 and a second cutting edge 46, along with a pair of opposed flanges 30—30 wherein one of the flanges has a beveled edge 32. Subsequently, a surgical opening is made through a skin tissue or knee capsule that surround a knee joint of a person who is being operated on. As is well known in the medical field, a knee joint comprises a posterior femoral metaphysis, a posterior femoral notch, a medial femoral condyle, a tibia, a lateral femoral condyle, and a distal femur. After the surgical opening has been made by way of an incision, the cutting end 20 is inserted through the surgical opening until the cutting edges 42 and 46 are disposed in the posterior femoral notch and against the lateral femoral condyle. The cutting end 20 should also be disposed such that the beveled edge 32 is pushed against the posterior femoral metaphysis. Subsequently, the guide wire 52 is inserted along and through the channel 48 in the shank back 16 of the surgical instrument and into the medial femoral condyle for implantment therein. The surgical instrument 10 is now in a position to perform the inside-out procedure to form the desired trough 21 in the femoral condyle 23. The inside-out procedure comprises a reciprocating action of pulling the surgical instrument 10 along the guide wire 52 until the cutting end means 20 leaves the surgical opening, cleating or removing femoral condyle bone debris from the cutting edges 42 and 46, and subsequently reinserting or pushing inwardly the surgical instrument through the surgical opening and along the guide wire 52 while the same is in the channel 48 until the cutting edges 42 and 46 are disposed over the location where the femoral condyle was previously cut by the cutting edges 42 and 46. The guide wire 52 serves as a means for registering and aligning the cutting end means 20 over the previously cut location on the femoral condyle 23. This inside-out procedure is repeated until the desired channel or trough 21 is formed having a suture channel 25 and a patellar bone block channel 27 that is disposed over and communicates with the suture channel, as best illustrated in FIG. 15.

The anterior cruciate ligament may be reconstructed by forming a patellar bone block having sutures that extend therefrom. One end of a patellar tendon (that has been previously removed from the front of the knee joint) is secured to the patellar bone block. The other end of the patellar tendon has secured thereto a tibia bone block with tibia sutures extending therefrom. The tibia bone block was obtained from the tibia and the tibia sutures are subsequently placed therein. A screw or pin means is inserted through the distal femur; and the sutures of the patellar bone block are disposed in the suture channel while the patellar bone block lodges in the bone block channel. Subsequently, the sutures of the patellar bone block are secured to the screw or pin means. Thereafter, the tibia bone block is resecured to the tibia by securing or attaching the tibia sutures to the tibia, which is typically done by stapling. The operation is now complete and the surgical opening may be sutured or otherwise closed.

Thus, the surgical instrument 10 of this invention creates the over-the-top trough 21 in the lateral femoral condyle 23 for mounting the anterior cruciate ligament. The channel 48 or slot in the back 16 of the shank 12 allows the initial position of the surgical instrument 10 utilizing the guide wire 52. As the trough 21 deepens, the shank 12 of the surgical instrument 10 tends to fall away from the guide wire 52 while in the trough 21; this is one of the primary reasons the channel 48 has been devised instead of a conventional enclosed hole which does not allow cutting into the femoral condyle 23 to a desired depth without removing the guide wire 52 and reinserting the same into the medial femoral condyle. The guide wire 52, as indicated above, is placed across the posterior femoral notch and into the medial femoral condyle and is subsequently removed after the trough 23 has been cut with the cutting edges 42 and 46. The opposed flanges 30—30 can control the depth of the trough 21 to any desired depth, depending on the thickness of the flanges. Typically, the depth of the trough is from approximately 3 mm to aobut 7 mm, preferably 5 mm. This depth is the same thickness as the formed patellar bone block and patellar tendon which will go into the trough 21. The two flanges 50—50 are shaped differently to follow cross section contour of the posterior femoral metaphysis (the beveled edge 34) and the lateral femoral condyle (the flange 50 having the rounded edge 34). As illustrated in the drawings, the top plan view of the flanges 50—50 illustrates the flanges 50—50 tapering to allow correct fit into the posterior femoral notch. The length from the cutting edges 42 and 46 to the planar surface 38 of the surgical instrument 10 is chosen to allow the proper fit in generally all posterior notches; and yet allow positioning of the surgical instrument 10 by a probe from anterior to posterior through the femoral notch. As has been previously mentioned, the cutting member 44 is smaller than the cutting member 40, and the former cutting member is forming the suture channel in order to make space available for the patellar bone block fixation sutures and for preventing the bulk of the suture bundles from holding the patellar bone block outside of the trough 21. The pin 26 that slidably passes into the aperture 24 of the handle end means 22 allows the use of a commercially available split or slap hammer to pull the surgical instrument towards the operator. This clears the bone debris out of the trough 21 and lessens the risk of loose bone particles in the knee. Thus, by the practice of this invention, there is provided a method for cutting over-the-top trough for proximal placement of patellar tendon graft for anterior cruciate ligament, and reverse cutting osteotome instrument therefor. The methods of this invention use an inside-out procedure, and not the typical or conventional outside-in procedure, well known to those skilled in the art. The inside-out procedure osteotome allows for more accurate positioning, while the flanges 30—30 control the depth of the trough 21 and while simultaneously adjusting the position from the top posterior outlet. The inside-out procedure cutting of this invention allows the bone debris resulting from the cutting to be removed. The planar surface 38 (i.e., the blunt end of the osteotome) allows for accurate entry into the over-the-top route and simultaneously protects the posterior cruciate ligaments. These anterior cruciate ligaments are the ligaments that are replaced by use of the osteotome or surgical instrument 10 of this invention. The cutting edges 42 and 46 of the osteotome or surgical instrument 10 allow for easy and rapid cutting away of hard bone from the femoral condyle.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A surgical instrument comprising a shank means having a pair of shank sides, a shank back and a shank front and a cutting end means and a handle end means; said cutting end means having a pair of grooves in said shank front and along said pair of shank sides such that said cutting end means has a structure defining a pair of opposed flanges; said shank back having a back channel; a first cutting member secured on said shank front at said cutting end means; and a second cutting member superimposed on said first cutting member and secured thereto.

2. The surgical instrument of claim 1 wherein one of said opposed flanges has a structure defining a beveled edge.

3. The surgical instrument of claim 1 wherein said back channel extends in said shank back along the suture thereof and terminates in an open channel end.

4. The surgical instrument of claim 1 wherein said first cutting member has a first cutting edge and said second cutting member has a second cutting edge that is substantially parallel with respect to the first cutting edge.

5. The surgical instrument of claim 4 wherein said first cutting edge is longer than said second cutting edge.

6. The surgical instrument of claim 1 wherein one of said flanges is formed with a rounded corner.

7. The surgical instrument of claim 1 wherein said handle end means has a structure defining a handle aperture.

8. A method for reconstructing an anterior cruciate ligament of a person comprising the steps of:
    (a) forming a surgical instrument having a channel in the back thereof and a cutting end means with a first cutting edge, a second cutting edge generally parallel to the first cutting edge, and a pair of opposed flanges wherein one of the flanges has a beveled edge;
    (b) forming a surgical opening through a skin tissue that surrounds a lance joint of a person, wherein said lance joint comprises a posterior femoral metaphysis, a posterior femoral notch, a medial femoral condyle, a tibia, a lateral femoral condyle, and a distal femur;
    (c) inserting the cutting end means through the surgical opening until the first and second cutting edges are disposed in the posterior femoral notch against the lateral femoral condyle and the beveled edge is flushed against the posterior femoral metaphysis;
    (d) inserting a guide wire through the channel of the surgical instrument and into the medial femoral condyle; and
    (e) pulling the surgical instrument along the guide wire causing the first cutting edge and the second cutting edge to cut and remove lateral femoral condyle bone fragments.

9. The method of claim 8 additionally comprising cleaning the removed lateral femoral condyle bone fragments from the first and second cutting edges.

10. The method of claim 8 additionally comprising moving through the surgical opening the surgical instrument along the guide wire while the same is in the channel until the first and second cutting edges are against the lateral femoral condyle again and repeating step (e).

11. The method of claim 10 additionally comprising repeating the steps of claim 10 until a suture channel is formed in the lateral femoral condyle and a bone block channel is also formed in the lateral femoral condyle imposed to the suture channel.

12. The method of claim 11 additionally comprising forming a patellar bone block having sutures and an end of a patellar tendon secured thereto.

13. The method of claim 12 additionally comprising forming a tibia bone block with tibia sutures and having another end of the patellar tendon secured to the tibia bone block.

14. The method of claim 13 additionally comprising inserting a screw means through said distal femur; disposing said sutures of said patellar bone block in said suture channel and said patellar bone block in said bone block channel; and securing said sutures to said screw means.

15. The method of claim 14 additionally comprising securing said tibia bone block to said tibia; and securing said tibia sutures to said tibia.

16. The method of claim 15 additionally comprising closing the surgical opening.

17. A method for forming a channel in a femoral condyle of a lance joint of a person comprising the steps of:
(a) forming a surgical instrument having a channel in the back thereof and a cutting end means with a first cutting edge, a second cutting edge generally parallel to the first cutting edge, and a pair of opposed flanges wherein one of the flanges has a beveled edge;
(b) forming a surgical opening through a skin tissue that surrounds a lance joint of a person, wherein said lance joint comprises a posterior femoral notch, a femoral metaphysis, a medial femoral condyle, and a femoral condyle;
(c) inserting the cutting end means through the surgical opening until the first and second cutting edges are disposed in the posterior femoral notch against the femoral condyle and the beveled edge is flushed against the femoral metaphysis;
(d) inserting a guide wire through the channel of the surgical instrument and into the medical femoral condyle; and
(e) pulling the surgical instrument along the guide wire outwardly and subsequently pushing inwardly the surgical instrument along the guide wire until the first cutting edge and the second cutting edge have cut a channel in the femoral condyle.

18. The surgical instrument of claim 6 wherein the rear of one of the flanges opposed to the flange with the beveled edge has a round edge.

19. The surgical instrument of claim 18 wherein said flange having said rounded edge has said rounded corner.

* * * * *